United States Patent [19]

Kolen

[11] Patent Number: 5,350,414
[45] Date of Patent: Sep. 27, 1994

[54] LOCAL APPLICATION MICROPROCESSOR BASED NERVE AND MUSCLE STIMULATOR

[75] Inventor: Paul T. Kolen, Carlsbad, Calif.

[73] Assignee: Electro Science Technologies, Inc., Las Vegas, Nev.

[21] Appl. No.: 139,872

[22] Filed: Oct. 22, 1993

Related U.S. Application Data

[63] Continuation of Ser. No. 804,455, Dec. 10, 1991, abandoned.

[51] Int. Cl.[5] ............................................. A61N 1/36
[52] U.S. Cl. .......................................... 607/62; 607/46; 607/59; 607/63
[58] Field of Search .................. 607/46, 59, 62, 63

[56] References Cited

U.S. PATENT DOCUMENTS

| | | | |
|---|---|---|---|
| 3,565,080 | 2/1971 | Ide et al. | 128/422 |
| 4,062,365 | 12/1977 | Kameny | 128/42 |
| 4,147,171 | 4/1979 | Greene et al. | 128/421 |
| 4,165,750 | 8/1979 | Aleev et al. | 128/422 |
| 4,167,189 | 9/1979 | Tachi et al. | 128/421 |
| 4,210,150 | 7/1980 | James | 128/421 |
| 4,210,151 | 7/1980 | Keller, Jr. | 128/421 |
| 4,324,253 | 4/1982 | Greene et al. | 128/421 |
| 4,338,945 | 7/1982 | Kosugi et al. | 128/421 |
| 4,340,063 | 7/1982 | Maurer | 128/421 |
| 4,387,718 | 6/1983 | Bilitz et al. | 128/419 R |
| 4,408,608 | 10/1983 | Daly et al. | 128/421 |
| 4,431,002 | 2/1984 | Maurer et al. | 128/422 |
| 4,509,520 | 4/1985 | Dugot | 128/421 |
| 4,524,773 | 6/1985 | Fischell et al. | 128/421 |
| 4,528,984 | 7/1985 | Morawetz | 128/421 |
| 4,535,777 | 8/1985 | Castel | 128/421 |
| 4,582,063 | 4/1986 | Mickiewicz et al. | 128/421 |
| 4,598,713 | 7/1986 | Hansjurgens et al. | 128/421 |

(List continued on next page.)

FOREIGN PATENT DOCUMENTS

0391428 10/1990 European Pat. Off. .
9014127 11/1990 World Int. Prop. O. .

Primary Examiner—William E. Kamm
Attorney, Agent, or Firm—Fish & Richardson

[57] ABSTRACT

A transcutaneous electroneural stimulation (TENS) device employing microprocessor control of carrier pulse frequency, modulation pulse frequency, intensity, and frequency/amplitude modulation factors has been developed. The microprocessor monitors battery status and keypad-entered commands that select the various TENS modalities, and generates the driver signals to produce the output waveform provided to a utilization device via a transformer arrangement. The microprocessor is programmed to calculate all stimulation parameters which are stored in nonvolatile memory to provide concise and predictable programmed functions which can be updated as required. By selecting a program, the system may be programmed to relieve pain or reduce edema in the application area. Thus, a variety of therapeutic applications may be realized. The output pulse train employs a unique pulse modulation scheme which matches the carrier frequency to the electrode-tissue load for location specific applications. By pulse modulating the high frequency carrier and matching the carrier frequency to the electrode-tissue load, a more efficient energy transfer is realized. This matching significantly reduces the required amplitude of the electrode voltage pulse and reduces the overall power requirements for the system. In addition to enhanced power efficiency, the unpleasant burning sensation associated with most TENS stimulation units is virtually eliminated. The unit can be integrated into a hermetically sealed miniaturized composite package which allows the unit to be worn in a non-interfering manner at the treatment location.

23 Claims, 6 Drawing Sheets

U.S. PATENT DOCUMENTS

| | | | |
|---|---|---|---|
| 4,640,286 | 2/1987 | Thomson | 128/421 |
| 4,671,286 | 6/1987 | Renault | 128/422 |
| 4,676,246 | 6/1987 | Korenaga | 128/399 |
| 4,693,254 | 9/1987 | Mickiewicz et al. | 128/421 |
| 4,723,552 | 2/1988 | Kenyon et al. | 128/421 |
| 4,759,368 | 7/1988 | Spanton et al. | 128/421 |
| 4,793,353 | 12/1988 | Borkan | 128/421 |
| 4,813,418 | 3/1989 | Harris | 128/421 |
| 4,832,033 | 5/1989 | Maher et al. | 128/421 |
| 4,890,616 | 1/1990 | Pinckaers | 128/419 R |
| 4,895,153 | 1/1990 | Takeuchi et al. | 128/421 |
| 4,917,092 | 4/1990 | Todd et al. | 128/421 |
| 4,919,139 | 8/1990 | Brodard | 128/421 |
| 4,922,906 | 5/1990 | Takeuchi et al. | 128/421 |
| 4,922,908 | 5/1990 | Morawetz et al. | 128/422 |
| 4,926,865 | 5/1990 | Oman | 128/421 |
| 4,938,223 | 7/1990 | Charters et al. | 128/421 |
| 4,976,264 | 12/1990 | Petrofsky | 128/421 |
| 4,977,895 | 12/1990 | Tannenbaum | 128/421 |
| 5,033,468 | 7/1991 | Takeuchi et al. | 128/421 |
| 5,036,850 | 8/1991 | Owens | 128/421 |
| 5,041,974 | 8/1991 | Walker et al. | 128/421 |
| 5,052,391 | 10/1991 | Silberstone et al. | 128/422 |
| 5,063,929 | 11/1991 | Bartelt et al. | 128/421 |

FIG. 8
$I_S$
40 mA/DIVISION

V
20 V/DIVISION

→ t  20 ms/DIVISION

FIG. 9
$I_S$
40 mA/DIVISION

V
20 V/DIVISION

→ t  20 ms/DIVISION

LOCAL APPLICATION MICROPROCESSOR BASED NERVE AND MUSCLE STIMULATOR

This application is a continuation of Ser. No. 07/804,455, filed Dec. 10, 1991, now abandoned.

BACKGROUND OF THE INVENTION

1. Field of the Invention

This invention is directed to a TENS-type therapeutic device, in general, and to a microprocessor controlled TENS-type system, in particular.

2. Prior Art

U.S. Pat. No. 4,926,865 issued to Oman discloses a transcutaneous nerve stimulation device which is microcomputer controlled and includes input controls for controlling pulse parameters. The background discussion of this patent offers a good overview of the history of induced nerve stimulation and is therefore substantially reproduced below.

The use of electrical energy for the control of pain is well known. Although the specific physiological explanations underlying electrically derived pain control are not fully understood, the effects are quite real and provide a non-drug, non-surgical and non-psychiatric method of pain control which can be applied to a wide variety of painful conditions.

Transcutaneous electroneural stimulation (TENS) is a proven and accepted means of providing relief from many kinds of acute and chronic pain symptoms. It is an attractive alternative to pharmaceuticals since it has no addictive properties. In addition, there are no known side effects to properly applied TENS therapy.

Several theories have been developed to explain the neuro-physiological mechanisms through which TENS can affect pain perception. The earliest accepted explanation is the gate control theory, first postulated by Melzack and Wall in 1965 (Melzack, R. Wall P. D., "Pain mechanisms: a new theory," Science, Vol. 150, pp. 971-979, 1965). This theory used data from animal experiments to predict that stimulation of afferent nerves could inhibit transmission from both noxious and non-noxious inputs. However, subsequent research with commercially available stimulators has demonstrated that TENS efficacy cannot be explained by gate control theory alone (Schmidt R. D., "Presynaptic inhibition in the vertebrate central nervous system," Ergebn. Physicol., Vol. 63 pp. 20-86, 1971).

More recent studies (Eriksson, M. B. E., Sjolund, B. H. and Nielzen, S., "Long term results of peripheral conditioning stimulation as an analgesic measure in chronic pain, " Pain, Vol. 6, pp. 335-347, 1979) have shown that TENS efficacy can be greatly enhanced for some patients by supplementing new stimulation techniques when unsatisfactory results are obtained with conventional stimulation. One popular technique incorporates experience from Chinese electroacupuncture. The discovery that the effects of this technique, as well as those from acupuncture, can be reversed with an opioid antagonist, e.g. naloxone hydrochloride (Sjolund, B. H. and Eriksson, M. B. E., "The influence of naloxone on analgesia produced by peripheral conditioning stimulation", Brain Res., Vol. 173, pp. 295-301, 1979, and Mayer, D. J., Price, D. D., and Rafii, A., "Antagonism of acupuncture analgesia in man by the narcotic atagonist naloxone", Brain Res., Vol. 121, pp. 368-372, 1977) suggested the possibility of an endogenous opiate system responsible for pain control.

Since 1975, several endogenous, morphine-like peptides have been isolated (Hughes, J. et al, "Identification of two related pentapeptides from the brain with potent opiate agonist activity", Nature, Vol. 258, p. 577, 1975), including endorphins which have been found in numerous locations within the central nervous system (Matsukura, S. et al, "The regional distribution of immunoreactive beta-endorphin in the monkey brain", Brain Res., Vol. 159, p. 228, 1978).

The above results have led some researchers (Eriksson, M. B. E., Sjolund, B. H., and Nielzen, S., "Long term results of peripheral conditioning stimulation as an analgesic measure in chronic pain", Pain, Vol. 6, pp. 335-347, 1979) to the conclusion that more than one neurophysiological mechanism is involved in modulating through transcutaneous stimulation. This theory is supported by clinical studies (Mannerheimer, J. S. and Lampe, G. N., "Clinical transcutaneous electrical nerve stimulation", F. A. Davis Company, Philadelphia, pp. 345-348, 1984) that demonstrate the different characteristics shown in Table 1 for conventional and acupuncture-like TENS.

TABLE 1

| Characteristics of TENS Modes | | | |
|---|---|---|---|
| Characteristic | Conventional | Acupuncture-like | Simultaneous bimodal |
| Intensity | low | high | combined |
| Rate | high | low | combined |
| Relief Onset | rapid | slow | rapid |
| Relief Duration | short | long | long |
| Accommodation | likely | unlikely | slight accommodation likely |
| Naloxone Reversible Effects | no | yes | reduced effects |

The listed properties for simultaneous bimodal stimulation (i.e. combined stimulation modes) use different stimulation mechanisms and suggest that the effects are additive. The validity of this assumption has been demonstrated in case studies (Mannheimer, J. S. et al. above), but more comprehensive research is needed.

Researchers have found that relevant electrical signal characteristics which must be examined in attempting to treat a painful sensation include the signal waveform, pulse repetition frequency, pulse duration, pulse amplitude and pulse modulation characteristics.

PRIOR ART STATEMENT

U.S. Pat. No. 4,210,151, Keller, discloses an example of a device which attempts to treat pain by electrode stimulation based on these principals. The Keller device employs a scanning oscillator which varies the pulse duration, pulse frequency and pulse amplitude. This repetitive variation of parameters guarantees that, at least for some small portion of the duty cycle, the optimum nerve stimulation conditions are achieved.

U.S. Pat. No. 4,340,063, Maurer, discloses a nerve stimulation device in which the amplitude of the pulse decreases with a degradation in pulse width along a curve defined by a hyperbolic strength-duration curve for living tissue. The imitation of this particular waveform results in a proportionately greater recruitment of nerve fibers due to the nonlinear relationship between pulse width and threshold.

The foregoing references are included by way of presentation of the background of the invention and do not constitute the inventive concept of the present application.

SUMMARY OF THE INVENTION

The invention is directed to the application of improved TENS system technology employing miniature electronic circuit components to provide a device that can be integrated into a variety of application-specific forms that will be operated at specific treatment sites on the human body. A unique TENS pulse technique has been developed which significantly reduces the power and the peak voltage requirements at the treatment site. This significantly reduces or eliminates the unpleasant burning of the skin under the electrodes typically experienced when using most currently available TENS units.

The invention uses commercially available electronic components. Low-profile, surface-mount components are used in all units integrated into the hermetically sealed treatment packages associated with the invention. A rechargeable, dry, electrolytic battery can be installed in the package to obtain at least eight hours of operation from a single charge. All external control signals, including ON/OFF, are keypad entered and put into effect by interaction with a single central processing unit (CPU). The CPU is programmed with application-specific waveform generating routines. Most treatment locations require a custom program. Inputs from the user are interfaced to the CPU where preprogrammed instructions are carried out.

As an optional feature to the basic unit, preprogrammed routines are stored in a memory, for example, an EEPROM, which can be altered or replaced as required by interfacing a PC computer or other dedicated controller via an on-board serial interface. Eight (8) tactile membrane switches can be accessed by the user to cause changes in the operation of the unit. The switches are configured as follows:

Two (2) switches to increase/decrease fixed intensity;
Two (2) switches to increase/decrease fixed modulation frequency;
One (1) switch to activate/de-activitate modulation frequency dither;
One (1) switch to activate/de-activitate intensity dither; and
Two (2) switches to turn ON/OFF the power to the unit.

Additional switches can be added to increase program features. Each operation of a switch will cause a single incremental change in the selected parameter. If the switch remains closed there will be no further changes in the parameters. This is a safety feature of the unit which prevents the application of a full power signal to the electrodes in the unlikely event a switch were to remain activated.

A unique pulse train generated from signals being developed by the CPU has been invented. The high frequency carrier is selected to match the TENS output circuitry to the electrode/tissue load at the treatment site. It has been noted that low frequency pulse modulation of a high frequency carrier signal penetrates the surface of the skin more easily due to capacitive coupling than the direct application of the low frequency modulating frequency, per se. As a consequence, a lower amplitude pulse can produce the equivalent effect at the treatment site. Because the energy from the modulated pulse is not dissipated in the skin, the presence thereof has virtually no effect on the skin. This reduces or eliminates irritating and annoying sensations on the skin while effecting treatment, as desired. The inherent power efficiency of this technique results in a longer battery life as an added benefit.

In one embodiment, an electronic package containing all components can be mounted within a sealed unit made of neoprene, Lycra Spandex, or other flexible material. The battery which powers the unit can be installed within the sealed unit and charged using an external charger. The TENS unit is not intended to be used when the charger is connected to the battery. The electronic circuitry is, preferably, constructed on a flexible printed circuit board (PCB). This PCB can be shaped into a form that complies with the requirement for the site specific treatment device.

Thus, the device consists of the electronic package, electodes and any appurtenances required to attach the unit to the treatment area. The overall unit is made so that it can be worn comfortably for an extended period during normal human activity.

DESCRIPTION OF A PREFERRED EMBODIMENT

Figure 1:
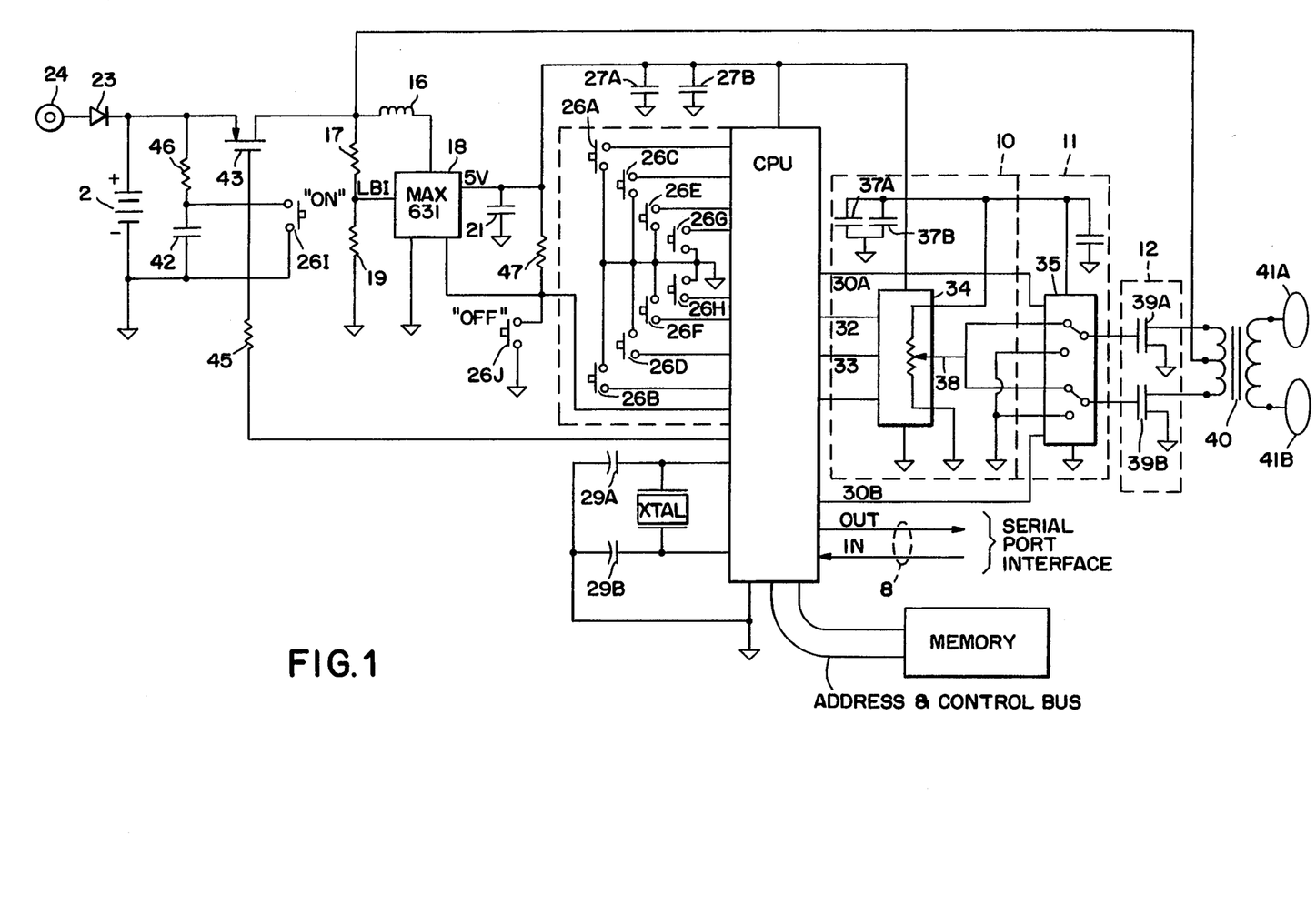
FIG. 1 is a schematic diagram of a preferred embodiment of the stimulator of the instant invention.

Referring now to FIG. 1, there is shown a partially block, partially schematic diagram of a TENS unit 10 according to a preferred embodiment of the instant invention. The data processing functions of the instant invention are performed by a microcomputer or CPU 1 which is, preferably, a single integrated circuit data processing chip. In a preferred embodiment, the CPU 1 includes memory 12. The memory can take the form of an electrically erasable, programmable, read-only memory (EEPROM). While not limited thereto, the CPU 1 is, preferably, a stand alone, high performance single-chip micro-controller fabricated in +5 volt advanced CMOS technology so as to provide low power consumption along with high speed operation. In the preferred embodiment, CPU 1 is an 68HC11E9 device which is available from several manufacturers and supplies the hardware features, architectural enhancements and instructions that are necessary for this invention. The memory 12 is used by the CPU 1 for storage of the waveform generation programs and interface/"house-keeping" routines required by CPU 1. (In some instances, it is possible to use static random access memory (SRAM) as the external memory.)

All operations of the preferred embodiment of the invention are carried out through interaction with CPU 1. As noted above, CPU 1 is preferably of the CMOS-type that is characterized by having an internal control processor unit (CPU), internal oscillator and timing circuits, 256 bytes of internal RAM, 64 Kbyte bus expansion control, five programmable I/O parallel ports for address, data bus and I/O pins, two 16-bit timer event counters and a programmable serial port with a full duplex universal asynchronous receiver and transmitter (UART) and synchronous shifter. These components are not delineated in detail herein.

The unit 10 is powered by a rechargeable nickel-cadmium battery 2. Typically, the battery 2 is of a sealed construction and can be encapsulated within a hermetic housing (not shown) of the stimulator package. An external battery charger (not part of the invention, per se) is used to "re-charge" the battery.

The battery charger is connected to the circuit in any suitable fashion such as, for example, via a jack 24. The jack 24 is connected to the battery 2 via a diode 23. Diode 23 is connected in series with battery 2 during the charge cycle and is used to prevent damage due to incorrect charging polarity. The charging current is controlled via feedback circuitry in the charging unit.

Battery 2, which can be composed of two standard rechargeable nickel-cadmium cells, provides 2.4 volts to a solid state power switch 14, which produces a regulated 5 volt output. In particular, an RC circuit comprising resistor 46 and capacitor 42 is connected across the battery. The anode of battery 2 is connected to the source electrode of a MOS switch 43. The gate electrode of MOS switch 43 is connected to the junction of resistor 46 and capacitor 42. The gate electrode is also connected to an output terminal 44 of CPU 1 (described infra). A Switch 26I (a break before make, momentary push button switch) is connected across capacitor 42. The drain electrode of MOS switch 43 is connected to the center tap of an electrode isolation transformer 40 and to the common terminal of an inductor 16 and a resistor 17. A DC-DC converter 18 operates as a voltage booster and maintains the required 5 volts signal. level at the output thereof by using an internal oscillator and solid state switch to switch inductor 16 in and out of the circuit. That is, when Vcc falls below the preset 5 volt value, an error comparator in the converter 18 gates on a 45 kHz oscillator which toggles an internal N-channel MOSFET ON/OFF.

When MOS gate 43 is ON, the switch closures in converter 18 during alternate half cycles connect the input voltage from the battery 2 directly across the inductor 16. This causes the inductor 16 to alternately charge from the input battery voltage and discharge at a higher voltage due to the collapse of the residual magnetic field at the inductor 16. The voltage is discharged into a filter capacitor 21. In order to maintain a constant voltage across capacitor 21 and load resistor 47, switching pulses are skipped in proportion to the number of switching cycles necessary to maintain the level of the output voltage at the preset level of 5 volts. One example of the converter 18 is a model MAX 631 manufactured by Maxim.

The other terminal of inductor 16 is connected to the input of DC-DC converter 18. The other terminal of resistor 17 is connected to ground via resistor 19. The common junction of resistors 17 and 19 is connected to another input of DC-DC converter 18.

Resistors 17 and 19 form a voltage divider which sets the threshold for activating a low battery indicator signal (LBI) at converter 18. The LBI signal is sent to the CPU 1. When a low battery signal is received, the power MOS gate 43 is released by the I/O pin 44 via software command. This causes the power to be removed from the circuit resulting in total shutdown until the batteries are recharged. This operation prevents the possibility of anomalous operation of the stimulator due to low battery voltage. The output of the converter 18 is about 5 volts regulated to stably operate the CPU 1 and the support circuitry of the stimulator.

A switch 26J (similar to switch 26I) is connected between an LBO terminal on converter 18 and ground or other suitable reference voltage. Switch 26J provides an OFF control for the power switch.

The solid state power switch 14 controls the activation of the system. For example, when the system is to be turned "ON", switch 26I is momentarily closed, thereby discharging capacitor 42 to ground. This drives the gate electrode of MOS switch 43 to ground, thus turning the MOS switch ON. When the MOS switch 43 is ON, voltage is applied to the converter 18 which produces +5 V and turns on the CPU 1. Once the CPU 1 is ON, the "initialize program" drives the output pin 44 low. With the output pin 44 low, the MOS switch 43 gate electrode is held low via resistor 45 even after switch 26I has been released. Resistor 46 and capacitor 42 form an RC time constant long enough to prevent the MOS switch 43 gate electrode from being pulled to +2.4 V via resistor 46 even if the switch 26I is released before the CPU 1 can hold the gate electrode low. The device is now actively held ON via the CPU 1.

Conversely, the power switch is turned "OFF" by momentarily closing switch 26J. Switch 26J is connected in parallel with the open drain output, LBO of the converter 18. Resistor 47 pulls LBO high unless a low battery level or switch 26J pulls LBO to ground. If LBO is detected low by the CPU 1, output pin 44 is set high via software, pulling the gate of the MOS switch 43 to +5 V. This causes the MOS switch 43 to turn OFF and remove the battery voltage from the power supply 14. This turns OFF the entire system. Resistor 46 keeps the MOS switch 43 gate electrode at +2.4 V and OFF even when the CPU 1 is OFF. The system can be restarted only by pressing switch 26J. No power is consumed when the system is OFF because terminal 44 is a high impedance when the CPU 1 is OFF.

Capacitors 27A and 27B are ceramic bypass capacitors which prevent transients from being conducted to other parts of the stimulator circuitry. In particular, capacitor 27A filters high frequency transients from the input power source to the CPU 1. Capacitor 27B provides the same function for lower frequencies that may be present on the power circuit due to switching transients from the converter 18 or interaction of the CPU 1 on the power circuit.

The CPU 1 is programmed to provide all the necessary functions for operator interface and output signal interfaces. Additionally, external communications with the controller are provided via serial communications link 8 that can be accessed for clinical and special application programming.

Typically, a user controller 20 of the TENS unit 10 includes any suitable devices, such as tactile membrane switches, that can be located either inside the sealed package or remotely, as required for application specific packages.

All user interfaces and input/output (I/O) functions are effected through the five parallel I/O ports and the serial port interface. In this embodiment, controller 20 comprises ten switches, typically in the form of a single 2×5 tactile membrane switch keypad. The keypad is used to control the operation of the unit 10 by providing a means of adjusting parameters through interaction of the switches with the user. These switches are configured as follows:

| 26A | Increase Fixed Intensity | 26B | Decrease Fixed Intensity |
| 26C | Increase Fixed Modulation Frequency | 26D | Decrease Fixed Modulation Frequency |
| 26E | Toggle ON/OFF Frequency Dither | 26F | Toggle ON/OFF Intensity Dither |
| 26G | Toggle ON/OFF Program 1 Dither | 26H | Toggle ON/OFF Program 2 Dither |
| 26I | ON Switch | 26J | OFF Switch |

Frequency reference for an oscillator 22 and associated timing circuits is provided by a piezoelectric crystal 25 mounted external to the CPU 1. Frequency control crystal 25, together with capacitors 29A and 29B form the external circuitry for the precision oscillator 22 which provides a stable frequency source for the operation of the timing and control functions of the CPU 1. The stable frequency source assures that frequency dependent functions, such as pulse width timing (PWT), will be consistent. The oscillator 22 functions as an integral part of the CPU 1. Capacitors 29a and 29b are selected to assure stable frequency operation at the desired frequency.

Memory 12 in the form of electrically eraseable programmable random memory (EEPROM) or static random access memory (SRAM) can be used as external memory for the CPU 1. Internal EEPROM as on the 68HC11 is the preferred memory for the purpose of this invention since program information recorded in the memory is retained during power off conditions and can be altered as needed. On the other hand, external EEPROM allows a larger program to be stored at the expense of more external circuitry.

Bi-phase signals are generated at terminals 30A and 30B of the CPU and supplied to a modulator switch 35. The up-down signal is supplied to a U/D terminal 32 and a digitally controlled potentiometer 34. The level of the U/D signal at the terminal 32 determines whether the potentiometer 34 will be increased or decreased. For example, high voltage level signals (+Vcc) at terminal 32 allow the potentiometer 34 to be incremented for an increase in resistance value. Thus, the potentiometer 34 is incremented one step at each transition of the increase signal (at terminal 33) from a high to a low level signal, e.g. from +Vcc to ground.

Conversely, by changing signal U/D from high to low, e.g. from +Vcc to ground, the potentiometer 34 is incremented to a lower resistance value by each high to low transition of a signal INC at terminal 33. The signal is supplied to a chip select pin of the potentiometer 34 to enable the potentiometer 34. When the potentiometer 34 is enabled, it is operative to store the current position setting in an internal non-volatile memory (NOVRAM) (not shown) within the potentiometer 34.

Capacitors 37a and 37b form a filter to eliminate switching transients that may be induced on the +Vcc power circuit and that would be sent into the input of the modulator switch and power drivers.

The voltage at an output terminal 38 is controlled by the position of the digitally programmed potentiometer 34 and is supplied to the modulator switch 35. Modulator switch 35 is a conventional CMOS transmission gate and provides a switching path which alternatively supplies first or second voltage levels to the gate electrodes of a set of power drivers 39A and 39B. More particularly, the switch 35 supplies a low (or ground) level signal to the power drivers 39A and 39B when the switch 35 is electrically connected to the ground (or other reference) terminals. Alternatively, the switch supplies a different (usually high) level signal to the power drivers 39A and 39B when the switch 35 is electrically connected to the output 38 of potentiometer 34.

The position of switch 35 is controlled by the signals from output lines 30A and 30B of the CPU 1. The voltage signal from switch 35 determines the amplitude and pulse width of the output signal supplied to the isolation transformer 40 by power drivers 39A and 39B. That is, battery 2 is connected to supply a positive voltage to the center tap 42 of the primary winding of transformer 40. The power drivers 39A and 39B are, typically, enhancement N-channel MOSFETS. The control voltages, Vgs, and the corresponding drain current, Id, of the power drivers are controlled by the voltage at terminal 38 which is switched through the switch 35.

An amplitude controller 24, which includes digitally controlled potentiometer 34, is used to control the amplitude of the signals produced by the CPU 1. In one embodiment, the controller 24 is a Xicor X9C503 which has 100 discrete, step-resistance values and provides a sufficiently high resolution for this application.

The modulator switch 35 can be a CD4053 analog transmission gate 28. The CPU 1 supplies digital control signals to switch 35 on line DC. Signals from the amplitude controller 24 are, thus, switched through the switch 35 in proper sequence and to the power drivers 39A and 39B and there used to drive the isolation transformer 40. The isolation (or matching) transformer 40 operates to supply the push-pull waveform generated by the power drivers 39A and 39B to the electrodes 41A and 41B. The trans-former 40 also provides a step-up in the level of the pulse voltage being sent to the electrodes 41A and 41B, if desired. It should be noted that electrodes 41A and 41B can vary in size and shape for each application.

Electrodes 41A and 41B are made from conducting rubber material and can be provided in appropriate size and shape for specific application configurations. These electrodes are connected to the output terminals of the secondary winding of transformer 40. Electrodes 41A and 41B are adapted to be applied to the body of the user in order to effect the proposed treatment.

Thus, in operation, the power switch 14 is turned ON (as described supra) to connect the battery 2 to the circuit in order to provide the appropriate power. The switches 26A through 26J are, selectively, activated to provide control signals to the CPU 1 (as described infra). The CPU 1 produces output signals which cause potentiometer 34 to increase or decrease incrementally. The potentiometer 34 supplies a selected voltage level to the switch 35. The switch 35 passes signals therethrough as a function of the signals from CPU 1. The voltage level passed by the switch 35 is applied to the power drivers 39A and 39B to control the signals therethrough and, thus, through the primary winding of transformer 40. The transformer 40 applies (via the secondary winding) the signals to the electrodes 41A and 41B. The electrodes provide the stimulation to the user to effect the desired treatment.

The user can control the treatment by selectively operating the individual switches 26A through 26H of the ontroller 20. As the switches are operated, the input to CPU 1 is changed whereupon the outputs therefrom are changed, as well. As a result, the signals at the electrodes 41A and 41B can be selectively controlled.

Due to the push-pull nature of the transformer drivers 39A and 39B, the AC voltage and current waveforms applied to the tissue are perfectly symmetrical in time and amplitude. This is important as waveforms that are net DC but not time symmetric will not result in net zero ion transfer. This is due to lighter ions carrying most of the current in the fast portion of the current pulse and light/heavy carrying the current in a slow pulse.

Figure 2A:
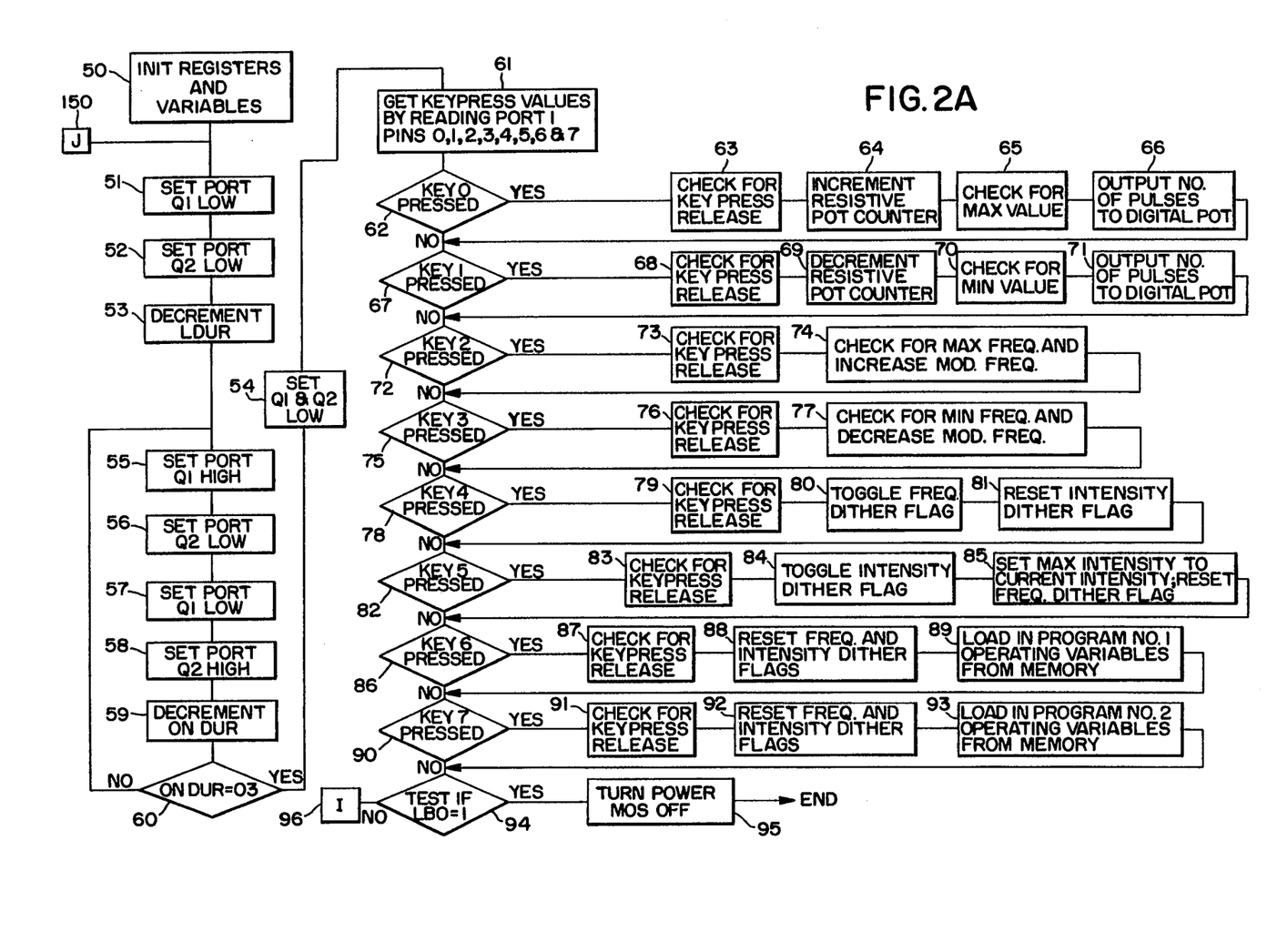
FIGS. 2A and 2B are logic flow charts that describe the functional sequencing of the invention.
Figure 2B:
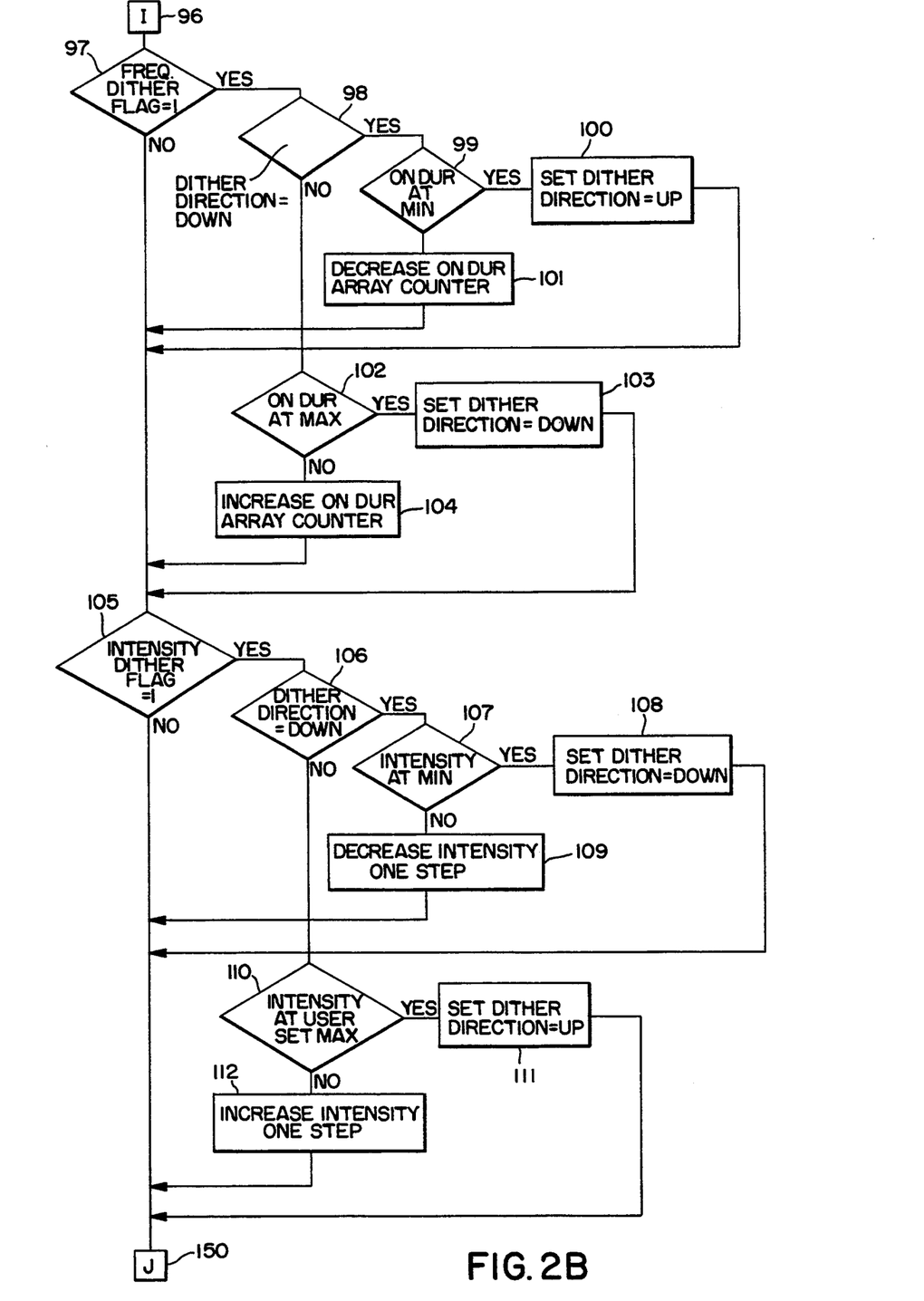

FIGS. 2A and 2B are flow charts which illustrate various functions performed by the CPU 1 during the operation of the present invention. In particular, referring concurrently to FIGS. 2A and 2B, there is shown the operation of the TENS unit 10. When power is initially applied to the CPU 1 at step 50, certain values are entered automatically so that no waveform will be produced by the stimulator. The next steps involve selection and initialization of various hardware and software options to be used to define certain ports as input or output, initialize output logic states, clear all working internal RAM bytes, define internal processor configurations and enable interrupts.

Thus, after the initialization of the processor at step 50, the program initiates the OFF cycle and, at steps 51 and 52, the driver ports Q1 and Q2 are set LOW. (Ports Q1 and Q2 correspond to terminals 30A and 30B on CPU 1 of FIG. 1.) The low level signals at ports Q1 and Q2 will inhibit any driver signals to the CMOS transmission gate electrodes by switch 35 during the OFF period.

Once the system is fully initialized, the program directs the system to steps 55 and 56, which set complementary ports Q1 and Q2, HIGH and LOW, respectively. This begins the ON duration (ONDUR) or stimulation generation subroutine during which a biphasic electrical stimulation is applied to the tissue via the step-up transformer 40 and electrodes 41A and 41B. The states of ports Q1 and Q2 are continuously reversed at steps 57 and 58 in a complementary manner for the duration of the operation until ONDUR=0.

At step 59, DECREMENT ONDUR, the high duration counter is decremented. If the ONDUR counter has not reached zero, the program will jump back to step 55 and go through the subroutine comprising steps 55 through 59 until the ONDUR counter has reached 0.

When ONDUR=0 is detected in step 60, the system jumps to step 54 and resets Q1 and Q2 low. Then it jumps to the subroutine represented by step 61 and begins to sequentially read the values in the controller 20 as supplied at input terminals 0 through 7 of CPU 1. Thus, the CPU 1 determines if any of the eight switches 26A through 26B has been pressed.

For example, if key 0 (which corresponds to switch 26A) is closed (or actuated), step 62 of the program will cause the JUMP Flag to be asserted. As a result, the system initiates the subroutine for increasing the intensity of the output signal at the electrodes 41A and 41B. In this subroutine, step 63 of the subroutine operates to check for keypress release. (It should be noted that the "check for keypress release" function in each subroutine automatically puts ports Q1 and Q2 in a low state, thereby effectively removing the stimulation signals until the key in question is released. Once released, the ports are reactivated and the program continues.) If the key 0 is closed at this time, the system will go to step 64 and operate to increment the counter in potentiometer 34. In carrying out this operation, the U/D terminal 32 of CPU 1 in FIG. 1 is set high (i.e. the signal U=+Vcc) and supplied to the digitally controlled potentiometer 34. The system then checks (at step 65) for the maximum value at the output of the digital potentiometer 34. If the potentiometer 34 is not at the maximum level as determined by a software counter, a predetermined number of pulses are supplied from the CPU 1 counter to the digitally controlled potentiometer 34 (at step 66) to increase the resistance thereof which effects an increase in amplitude of the output signal in accordance with the number of pulses. Typically, in this embodiment, there are 50 discrete steps available to the user.

The CPU 1 then returns to the main program and, at step 67, samples port 1 of CPU 1 to detect whether key 1 (switch 26B) has been pressed. If key 1 is pressed, the system initiates the decrease intensity subroutine. In this subroutine, the system checks for key press release at step 68 and then, at step 69, operates to decrement the resistive potentiometer 34. This step sets U/D terminal 32 to the low level, i.e. D=ground. This low level signal is supplied to the digitally controlled potentiometer 34. At step 70, the system checks for the minimimum value at the output of the potentiometer 34 via the software counter. If the system is not at the minimum value, step 71 of the subroutine causes a number of pulses to be supplied to digital potentionmeter 34, which will decrement. the potentiometer 34 and decrement the output signal intensity.

The system continues with the main program at step 72 and checks to see if the "key 2 pressed ?" condition exists. If key 2 is pressed, the program will initiate the increase fixed modulation frequency subroutine.

At step 73 of the subroutine, the system checks for keypress release. At step 74, the system operates to increment an array of values which are loaded into ONDUR to increase the fixed modulation frequency of the output signal. Typically, this is a "look-up table" routine which loads predetermined values into ONDUR to generate the designated modulation frequency such that a fixed number of pulses per second are generated. Typically, this value will range from 2 pulses per second to no pulses per second.

Once these steps are complete, the subroutine returns to the main program which, at step 75, determines if key 3 is pressed. If yes, the system operates the fixed modulation frequency decrease subroutine at steps 76 and 77. (This is similar to but the inverse of the frequency increase subroutine of steps 73 and 74.)

The program continues to step 78 to determine if key 4 has been pressed and, at step 79, determines if the key press has been released. If key 4 is pressed, the system will toggle the frequency dither flag from ON to OFF or OFF to ON, depending on the current state at step 80. At step 81, the intensity dither flag is reset to prevent both frequency dither and intensity dither from being active simultaneously.

The system is returned to the main program at step 82 to determine if key 5 is pressed. When key 5 is pressed, the program will run the intensity dither toggle subroutine. In this case, the system checks for keypress release (of key 5) at step 83 and toggles the intensity dither flag at step 84. At step 85, the maximum dither intensity is set to the current user set intensity and the frequency dither flag is reset. This prevents both intensity and frequency dither from being active simultaneously.

The subroutine then returns to the main program and checks to see if key 6 has been pressed at step 86. When key 6 is actuated, the program will execute a user program subroutine. This subroutine operates to check for keypress release at step 87, resets both the frequency and intensity flags at step 88, and loads the variables from memory to execute the user program at step 89.

When key 7 is actuated (see step 90), the action is identical to the key 6 actuated subroutine except that the variables from memory are to execute a second program. That is, keypress release of key 7 is checked at step 91; resets both the frequency and intensity dither flags at step 92; and loads the the second program operating variable from memory in step 93.

Next, the LBO state is tested in step 94. If LBO is low, the program is terminated by step 95.

After the "key check" steps have been completed (and LBO is not equal to 1), the system proceeds to the frequency dither subroutine at step 96, which is shown in FIG. 2B. This subroutine begins by checking the frequency dither flag set condition at step 97. If the frequency dither flag is not set, the subroutine goes immediately to the amplitude modulation subroutine described infra. If the flag is set, the subroutine checks to see if Dither Direction=DOWN at step 98. If yes, the subroutine goes to step 99 and checks if ONDUR is at minimum array value. If yes, the system goes to step 100 to set Dither Direction=UP. If no, the subroutine decrements the ONDUR array reducing the frequency at step 101.

However, if Dither Direction=UP at step 98, the subroutine goes to step 102 to check if ONDUR is at maximum array value. If yes, the system goes to step 103 to set Dither Direction=DOWN. If no, the subroutine increments the ONDUR array, increasing the frequency at step 104.

When the system enters the amplitude modulation subroutine noted above, it also checks to see if the intensity dither flag is set at step 105. If no, the subroutine will exit at terminal. J (step 150) and return to the primary program as shown in FIG. 2A.

If step 105 is yes, the subroutine will check to see if Dither Direction=DOWN at step 106. If yes, the subroutine will check if intensity is at the minimum value at step 107. If yes, the system goes to step 108 to set Dither Direction=UP and then returns to the main program at step 150 (see also FIG. 2A).

On the other hand, if step 107 indicates that the intensity is not at the minimum, the subroutine decreases the intensity at step 109 and returns to the main program at step 150.

In similar fashion, if the condition Dither Direction=UP (i.e. "NO" indication) is detected at step 106, the subroutine goes to step 110 to check if the intensity is at the maximum level set by the user of the device. If yes, the system goes to step 111 to set Dither Direction=UP. If no, the routine increases the intensity at step 112 and then returns to the main program at step 150.

As noted, terminal J (or step 150) is the start point for the main program to set port Q1 LOW wherein the sequence begins again. The main program and the several subroutines continue during operation of the stimulator until LBO=0 or the OFF button 26J is operated.

As noted supra, the switches 26A and 26B are complementary switches as are switches 26C and 26D. Thus, normally only one of each of these "sets" of switches will be operated at any time. For example, the output signal will be "increasing" or "decreasing". Thus, the appropriate action will be to "increment" or "decrement" the system. In like fashion, the "key pressed" detection steps are paired in sets. Consequently, it is considered typical that if "key 0 pressed" is detected, "key 1 pressed" will not be detected. Thus, alternate subroutines will be activated and the complementary subroutine will be skipped. For example, if the "increment" subroutine is activated because key 0 is pressed, it is expected that the "decrement" subroutine will not be activated because key 1 is not pressed. Thus, the system will jump directly from step 67 to step 72. The inverse operation is, of course, equally applicable.

Figure 3:
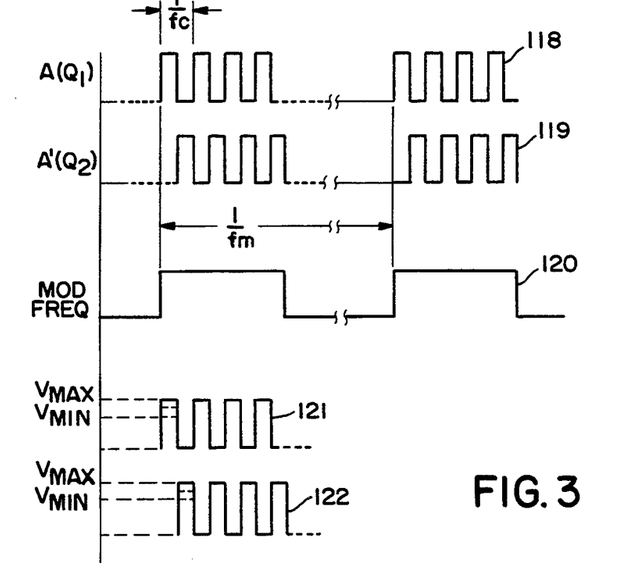
FIG. 3 is a graphic representation of the microprocessor generated ddriver waveforms produced by the invention.

Referring now to FIG. 3, there is shown a graphic representation of the output waveforms generated as the result of the program interaction in the CPU 1 in FIG. 1. The carrier waveforms, A and A' in FIG. 3 are bi-phase, complementary pulse signals 118 and 119 generated by a software subroutine within the CPU 1. Every time this subroutine is called, four cycles of the carrier frequency are applied to ports Q1 and Q2 in a complementary fashion. This carrier frequency ($f_c$) is preset in software to a specific predetermined frequency which is fixed, but load dependent. That is, the frequency is largely determined by the size and placement of the electrodes 41A and 41B in FIG. 1. Thus, as the electrode size and/or tissue varies, the load presented to the transformer secondary also varies. To allow maximum power transfer to the tissue load, the carrier frequency is adjusted such that $Z_{sec}=Z_L$ at that $f_c$. In a preferred embodiment, the carrier frequency is 1–2 KHz.

The modulation frequency subroutine of waveform 120 is user variable (typically from about 2 Hz to 100 Hz) and is selected by keys 26C and 26D shown in FIG. 1 and in accordance with the operation of steps 72 and 75 shown in FIG. 2A. The $f_c$ routine is "ANDED" with the $f_m$ routine in software. The pulse width of $f_m$ is ifxed to $4f_c$ with the resulting duty cycle or ON/OFF being variable.

The activation/de-activation of the frequency or intensity dither is controlled by keys 26E and 26F shown in FIG. 1 and the program operation of steps 78 and 82 shown in FIG. 2A. When the user presses key 26E or 26F (as detected at the steps 78 or 82), the dither function is either activated or de-activated. The duty cycle determines how many of the carrier pulses 121 are driven onto the electrodes during one $f_m$ period. This is an important parameter as it determines the average duration of the stimulating pulse and, together with the MOSFET gate voltage, determines the total energy transferred through the electrodes to the treatment site. In other words, when the modulation frequency signal 120 is ON, the waveforms A and A' pass through the gates 38A and 39B as waveforms B and B', respectively. These waveforms are shown as signals 121 and 122, respectively. Conversely, when the modulation frequency signal 120 is OFF, the waveforms A and A' are blocked and the signals B and B' remain at a prescribed level, e.g. ground. The amplitude of the drive pulses (i.e. signals 121 and 122) delivered to drivers 39A and 39B, respectively, is variable from Vmin (for example 2.1 V) to Vmax (for example 4.75 V) to thereby control the intensity of the stimulation. The amplitude of the signals 121 and 122 is, of course, controlled by the voltage level of the signal supplied by the potentiometer 34 as shown in FIG. 1. Thus, in this embodiment, fifty (50) discrete steps are provided.

It has been determined that the electrical load presented to the stimulator pulse is primarily capacitive. This capacitive effect is primarily the result of the high resistance exhibited by the surface of the skin.

Figure 4:
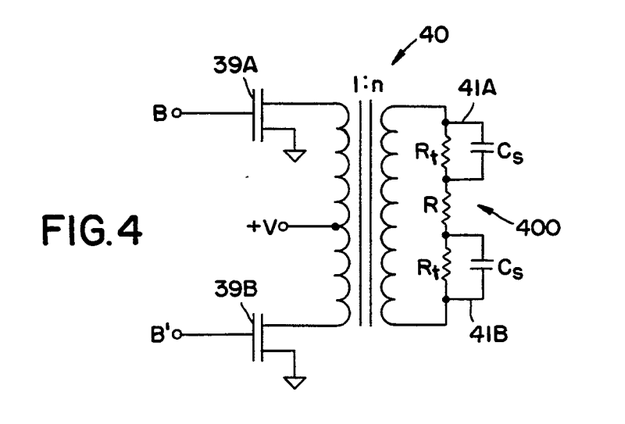
FIG. 4 illustrates a model of the output circuitry.

Referring now to FIG. 4, there is shown a circuit model of the instant invention as affected by human skin. In particular, the MOSFETS 39B and 39B receive the signals B and B', respectively, from the switch 35 as shown in FIG. 1. The MOSFETS drive the opposite ends of the primary winding of the transformer 40. The primary winding is a grounded center tapped winding. The opposite ends of the secondary winding (which is a 1:N ratio relative to the primary winding where N is greater than 1) is connected to the electrodes 41A and 41B, respectively. The electrodes 41A and 41B are placed on the skin of the user. The intermediate body portion (or "tissue load") of the user is schematically represented as the tissue load 400 between the electrodes. The tissue load 400 includes skin, muscle, nerve fibers and the like and is represented by the electrical analog comprising resistors Rs and Rt as well as capacitors Cs.

It is known that human skin exhibits a relatively high resistance to the flow of DC electrical current. Conversely, the subcutaneous tissue layers forming the muscles and nerve fibers of the body exhibit a relatively low resistance to the flow of either DC or AC electrical current. Thus, in this system, the electrodes 41A and 41B appear as plates of a capacitor having a lossy interelectrode dielectric which represents the tissue load 400.

Isolation/step-up transformer 40 (see also FIG. 1) is, preferably, electrically matched to the electrode/tissue load at the $F_c$ in order to realize an efficient transfer of electrical impulse energy to the inner tissue and nerve sites of the body. In the electrical model shown in FIG. 4, Rs is the skin bilayer resistance, Cs is the skin bilayer capacitance and Rt is the extracellular tissue resistance. For typical body applications, Rt is approximately 100 ohms wherein the electrical resistance of the tissue is dominated by Rs, which is on the order of 10 K ohms. Clearly, the values of Rs and Cs are determined by the electrode area and interface characteristics with the skin.

Figure 5:
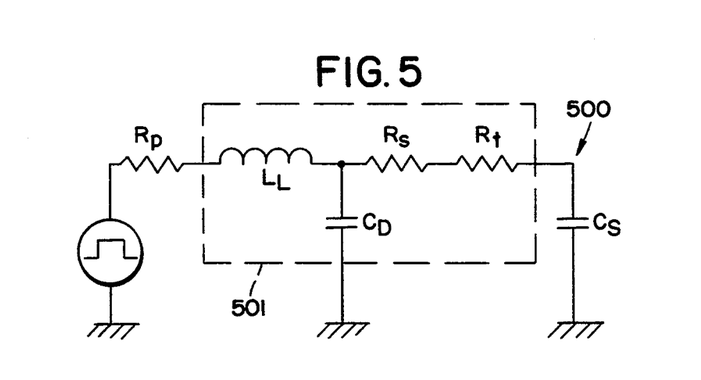
FIGS. 5 shows the electrical models of the stimulator waveform.

Referring now to FIG. 5 there is shown the primary-referenced equivalent load model 500 for the system shown in FIG. 1. This model represents the operation of the transformer 40 in the instant invention. The secondary DC resistance Rsec, the tissue resistance Rt, and the electrode/tissue capacitance Cs are "reflected" to the primary side of the transformer by the appropriate use of the turns ratio N. Because of the relatively low values of Rs and Rt, as well as the relatively large turns ratio (N) of the step-up transformer, the respective transformed values will be small compared to the value of primary DC resistance Rp. Consequently, these transformed values can be neglected in the analysis. Similarily, the values of leakage inductance $L_L$ and stray capacitance $C_D$ are also small and are also neglected. These assumptions lead to the simplified primary load model wherein the components within the dashed outline 501 are, effectively, deleted from consideration. Thus, it can be easily seen that the model reduces to a simple RC network comprising the primary DC resistance Rp and the reflected tissue capacitance $N^2 C_S/2$. This network is driven by a step voltage G of half period $f_c/2$, where $f_c$ is the carrier frequency. This reactive load determines the time it takes the primary to reach saturation. Thus, it determines, in large part, the total number of primary TURNS together with the range of obtainable carrier frequencies.

Figure 6:
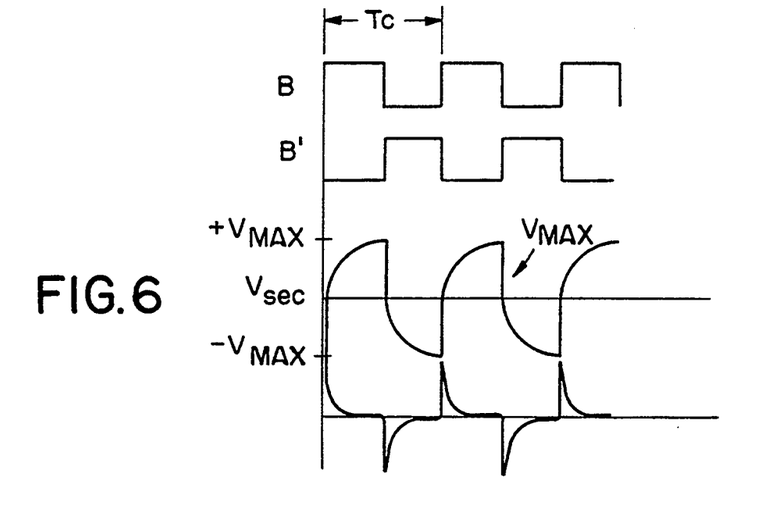
FIG. 6 is a graphic representation of the electrode/tissue current/voltage relationship.

It is known that nerve stimulation is effected by the flow of current through the extracellular tissue resistance Rt, not by the voltage impressed across the electrodes 41A and 41B. The maximum current flow in/out of the capacitor defined by the electrodes and, thus, through Rt, is at the maximum rate of charge of the voltage across the capacitor. This condition is illustrated in FIG. 6 together with timing relation to the microcontroller driver signals B and B'. It can be seen from the diagram that the carrier frequency fc must be adjusted to allow maximum saturation of the transformer core prior to the complementary reversal of B and B'. Thus, the maximum core saturation in transformer 40, coupled with the current reversal in the primary coil, creates a maximum rate of change in the secondary voltage Vsec and a corresponding maximum stimulation current Isec through the tissue load Rt. The selection of the optimum carrier frequency is highly dependent on the selected matching transformer and electrode geometry which controls Cs, as noted supra.

The secondary TURNS are determined to match the secondary impedance to the load impedance by an itterive process between the selection $f_c$, the number of primary TURNS and the TURNS ratio.

Figure 7:
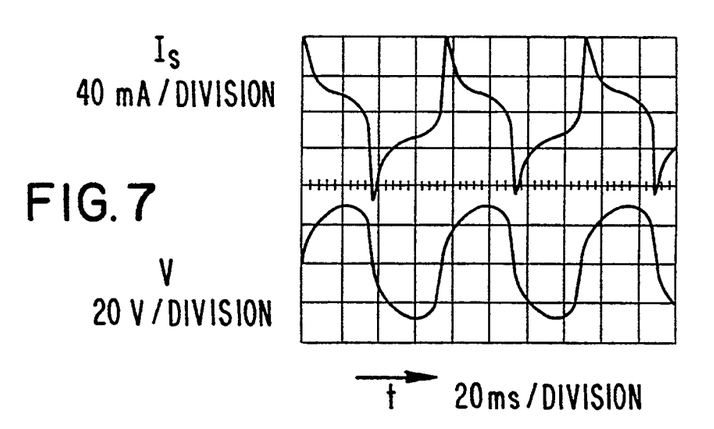
FIGS. 7, 8 and 9 are graphic representations of the output waveforms associated with critically saturated, under-saturated and over-saturated transformer operation.
Figure 8:
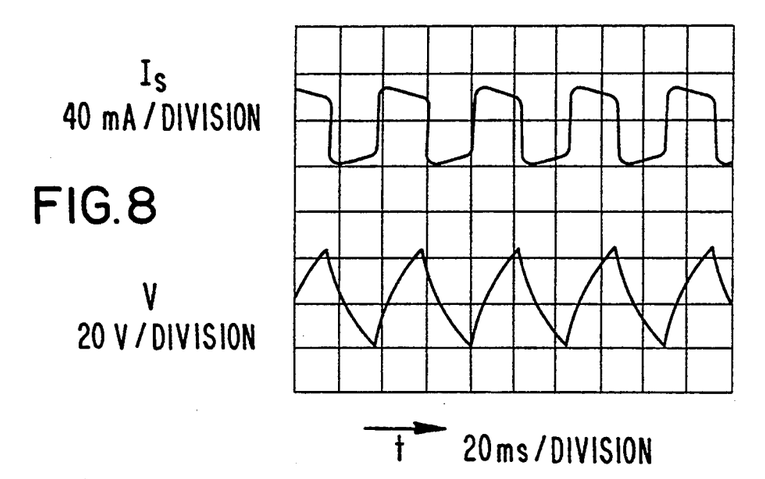
Figure 9:
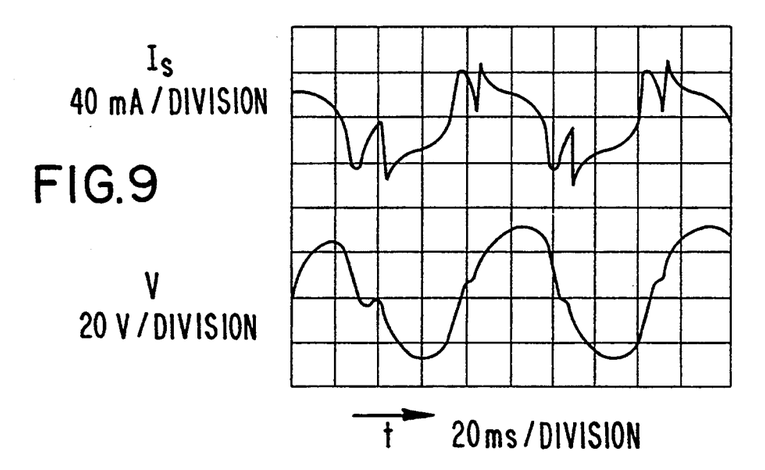

Referring now concurrently to FIGS. 7, 8 and 9, there are shown waveforms of critically saturated, critically under-saturated, and over-saturated operation of the matching transformer, respectively. In particular, FIG. 7 illustrates the maximum secondary load current Ismax attainable from optimum core saturation. The optimum saturation is the result of tuning $F_c$ to the OPTIMUM transformer/electrode/tissue load saturation period yielding maximum power transfer to the tissue load 400 for a given transformer configuration. Critical saturation operation is highly dependent on electrode/tissue capacitance and therefore, requires $f_c$ to be tuned to each electrode geometry as described above. In this case, $f_c$ is selected to be 535 Hz.

FIGS. 8 and 9 represent the operation of the identical circuit for which operation is illustrated in FIG. 7 but with $f_c$ adjusted above (913 Hz) and below (468 Hz) the optimum value, respectively. It can be seen in FIG. 8 that the peak and average secondary current is well below that obtained in FIG. 7. In FIG. 9 it is apparent that the transformer core became saturated with the primary current Ip limited by the DC series resistance and the same reduction in secondary current amplitude. When the transformer core becomes saturated, it ceases to operate as a transformer. At the point of core saturation, the secondary current goes to zero while the primary current goes to a high value which is determined by the supply voltage and the DC series resistance. The DC series resistance limits the primary current.

This invention develops a unique frequency and amplitude modulated pulse train. Because of the frequency modulation of the pulses, the stimulating signal can more easily penetrate the skin thus requiring a lower voltage to produce the same effect to the nerve and muscle tissue as most presently developed conventional stimulators. Also unique in this invention is the development of application-specific packages that can be worn and operated thereby permitting treatment during normal human activity. Conventional stiumlators now in use are not easily adapted to this type of application and this invention offers a definite advantage gained from this type of application. A very real advantage is that a person can realize the benefits of TENS treatment while engaged in normal day to day activity. The invention is developed from electronic components that are readily available from several manufacturers. This assures that the invention can be manufactured and become useful.

Thus, this invention provides a TENS unit employing a unique output waveform. The unit can be worn by persons undergoing treatment during normal daily or sports related activities. The unique output waveform reduces the power and voltage level requirements of the signal being applied to the treatment area thus significantly reducing or eliminating the uncomfortable burning sensation normally associated with most conventional TENS applications. The unit can be packaged such that all power sources, electronics, user interface electrodes and applications devices (such as wraps or specialty garments) can be contained in a single composite form. This form is, typically, application-specific and designed for a particular treatment locations, e.g., back, neck, leg, knee, ankle, hip, and the like. All active circuitry and power sources can be contained in a single hermetically sealed package designed to provide a maximum of safety and to facilitate ease of operation.

The above description shall not be construed as limiting the ways in which this invention may be practiced but shall be inclusive of many other variations that do not depart from the broad interest and intent of the invention.

Thus, there is shown and described a unique design and concept of a transcutaneous electric nerve stimulation (TENS) device. The particular configuration shown and described herein relates to electronic stimulators. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. An electrical stimulation device for applying a stimulation signal to living tissue, said electrical stimulation device comprising:
    pulse generating means for generating the stimulation signal, wherein the stimulation signal is a pulse train including a frequency and an amplitude component; and
    at least a pair of electrodes for contacting living tissue,
    wherein said pulse generating means includes a selector so that the pulse generating means is selectively operable to generate a carrier frequency of the pulse train in accordance with the size and placement of the electrodes such that the electrodes are impedance matched to the tissue.

2. The electrical stimulation device according to claim 1, said electrical stimulation device further comprising a transformer means for applying the stimulation signal to the electrodes and a driver means for driving the transformer means,
    wherein said transformer means becomes critically saturated by said driver means so that the pulses in the pulse train do not reach their peak voltage to prevent a DC component of the pulse train to be transferred to the tissue.

3. The electrical stimulation device according to claim 2, wherein said driver means comprises two FET switching transistors, the at least a pair of electrodes comprises two electrodes, and said switching transistors apply the pulse train to said two electrodes.

4. The electrical stimulation device according to claim 1, said electrical stimulation device further comprising controller means for controlling the parameters of the pulse train,
    wherein said controller means comprises:
        first means for adjusting an amplitude parameter of the pulse train,
        second means for adjusting a frequency parameter of the pulse train,
        third means for adjusting a frequency dither parameter of the pulse train, and
        fourth means for adjusting an intensity dither parameter of the pulse train.

5. The electrical stimulation device according to claim 1, wherein said pulse generating means is a microprocessor which generates a preprogrammed frequency and amplitude varied pulse train to the electrodes.

6. The electrical stimulation device according to claim 5, said electrical stimulation device further comprising memory means for storing pre-selected parameters of a pulse train stimulation signal, said memory means is connected to the microprocessor and said microprocessor selectively retrieves the stored parameters from said memory means.

7. The electrical stimulation device according to claim 1, said electrical stimulation device further comprising means for selectively adjusting an output voltage of the pulse train, said means for selectively adjusting an output voltage receives output signals from said pulse generating means which causes said means for selectively adjusting an output voltage receives to increase or decrease the output voltage in an incremental fashion.

8. An electrical stimulation device for applying a stimulation signal to living tissue according to claim 7, wherein said means for selectively adjusting an output voltage is a potentiometer.

9. The electrical stimulation device according to claim 1, said electrical stimulation device further comprising switch means for selectively applying a voltage to the electrodes, said switch means receiving a signal from said pulse generating means to cause said switch means to switch between the high or low voltage levels.

10. The electrical stimulation device according to claim 1, wherein the at least a pair of electrodes comprises two electrodes that apply a bi-phasic pulse train to the tissue.

11. The electrical stimulation device according to claim 1, said electrical stimulation device further comprising a battery and a low battery detect circuit means for indicating to said pulse generating means that said electrical stimulation device is at low battery power.

12. An electrical stimulation device for applying a stimulation signal to living tissue according to claim 11, wherein said transformer means becomes critically saturated when the output voltage equals ninety percent of the maximum voltage.

13. An electrical stimulation device for applying a stimulation signal to living tissue, said electrical stimulation device comprising:

pulse generating means for generating the stimulation signal, wherein the stimulation signal is a pulse train including a frequency and amplitude component; and a transformer means for applying the stimulation signal to at least a pair of electrodes and a driver means for driving said transformer means, the electrodes contacting the living tissue, wherein said transformer means becomes critically saturated by said driver means such that the pulses in the pulse train do not reach their peak voltage to prevent a DC component in the pulse train to be transferred to the tissue.

14. The electrical stimulation device according to claim 13, said electrical stimulation device further comprising controller means for controlling the parameters of the pulse train, wherein said controller means comprising:

first means for adjusting an amplitude parameter of the pulse train, second means for adjusting a frequency parameter of the pulse train, third means for adjusting a frequency dither parameter of the pulse train, and fourth means for adjusting an intensity dither parameter of the pulse train.

15. The electrical stimulation device according to claim 13, wherein said pulse generating means is a microprocessor which generates a preprogrammed frequency and amplitude varied pulse train to the electrodes.

16. The electrical stimulation device according to claim 15, said electrical stimulation device further comprising memory means for storing pre-selected parameters of a pulse train stimulation signal, said memory means is connected to said microprocessor and said microprocessor selectively retrieves the stored parameters from said memory means.

17. The electrical stimulation device according to claim 13, said electrical stimulation device further comprising a means for selectively adjusting an output voltage of the pulse train, said means for selectively adjusting an output voltage receives output signals from said pulse generating means which causes means for selectively adjusting an output voltage receives to increase or decrease the output voltage in an incremental fashion.

18. An electrical stimulation device for applying a stimulation signal to living tissue according to claim 17, wherein said means for selectively adjusting an output voltage is a potentiometer.

19. The electrical stimulation device according to claim 13, said electrical stimulation device further comprising switch means for selectively applying a voltage to the electrodes, said switch means receiving a signal from said pulse generating means in order to cause the switch means to switch between the high and low voltage levels.

20. The electrical stimulation device according to claim 13, wherein the at least a pair of electrodes comprises two electrodes that apply a bi-phasic pulse train to the tissue.

21. The electrical stimulation device according to claim 13, said electrical stimulation device further comprising a battery and a low battery detect circuit means for indicating to said pulse generating means that electrical stimulation device is at low battery power.

22. The electrical stimulation device according to claim 13, wherein said driver means comprises two FET switching transistors, the at least a pair of electrodes comprises two electrodes, and said switching transistors apply the pulse train to said two electrodes.

23. An electrical stimulation device for applying a stimulation signal to living tissue according to claim 13, wherein said transformer means becomes critically saturated when the output voltage equals ninety percent of the maximum voltage.

* * * * *